United States Patent [19]

Bursack et al.

[11] 4,201,913
[45] May 6, 1980

[54] SAMPLING SYSTEM FOR MASS SPECTROMETER

[75] Inventors: William W. Bursack; Erik T. Tromborg, both of Minneapolis, Minn.

[73] Assignee: Honeywell Inc., Minneapolis, Minn.

[21] Appl. No.: 949,295

[22] Filed: Oct. 6, 1978

[51] Int. Cl.² .................. B01D 59/44; H01J 39/34
[52] U.S. Cl. ............................... 250/288; 250/289
[58] Field of Search ............ 250/288, 289, 292, 441, 250/457; 313/7, 174, 231; 73/23

[56] References Cited

U.S. PATENT DOCUMENTS

| | | | |
|---|---|---|---|
| 3,801,788 | 4/1974 | Milne | 250/288 |
| 3,895,231 | 7/1975 | Sodal et al. | 250/288 |
| 3,992,626 | 11/1976 | Bursack | 250/288 |
| 4,023,398 | 5/1977 | French et al. | 250/288 |

Primary Examiner—Bruce C. Anderson
Attorney, Agent, or Firm—Charles G. Mersereau

[57] ABSTRACT

An apparatus for introducing a gaseous sample into a mass spectrometer is disclosed which includes a hollow antechamber or cavity disposed between the sample stream and the high vacuum enclosure. Orifice openings are provided in the antechamber which allow the antechamber to communicate both with the high vacuum enclosure and the sample stream. An electrically operated pulsed valve is used to admit a series of small volumes of sample by pulses of controlled duration and frequency such that the sample flow from the antechamber into the high vacuum enclosure can be made to resemble one of essentially constant flow.

4 Claims, 4 Drawing Figures

SAMPLING SYSTEM FOR MASS SPECTROMETER

BACKGROUND OF THE INVENTION

1. Field of the Invention

This invention relates to the field of gas analysis and, more particularly, to the control of the admission of samples and the control of subatmospheric sample pressures in the use of a mass spectrometer.

2. Description of the Prior Art

A mass spectrometer is an arrangement for sorting streams of electrified particles (ions) in accordance with their different masses by means of electric or magnetic fields which include a mass filter. It consists of a chamber to which the particles are caused to pass while being subjected to the coercing field, radio frequency or other means for establishing the field, means for receiving and detecting the arrival of particles after they have traversed the field and, a sampling system for applying the particles of material to be studied. The chamber must be maintained in a vacuum high enough such that it will result in a mean free path to the particles which is comparable with the distance they must travel for effective interaction with the fields. The fields are such that when particles of several different mass numbers are supplied to the chamber, only those of a particular mass number determined by the deflecting field are passed to be detected. All others are, in effect, rejected by the mass filter and never detected. If the low pressure in the chamber is to be maintained, the rejected particle must be removed from the chamber as rapidly as the particles are admitted. The field may be varied, however, so that particles of a number of predetermined masses, if present in the sample, reach the detecting means sequentially in an order determined by the field variation. This enables the mass spectrometer to determine more than one component in a given gaseous sample.

Mass spectrometers have been operated in continuous communication with a volume of gas whose composition is to be studied. Normally, the gas to be studied is maintained at atmospheric pressure (hereinafter referred to as a "sample gas" or as a "atmospheric gas" or "atmospheric sample"). In order to maintain the required mass spectrometer high vacuum, the continuous admission of the sample must be accompanied by continuous pumping or removal of an amount equal to that admitted. To avoid unreasonable pumping requirements, it is customary to provide a limiting input device between the volume of sample gas to be studied and the spectrometer chamber. In the prior art such input devices have included certain pressure dropping arrangements such as capillary tubes, porous elements and exceeding minute apertures. These arrangements continuously permit sample gas to enter the chamber and determine the rate of gas entry and hence the required pumping capacity necessary to maintain the desired vacuum.

For practical pumping rates, the volume of a suitable capillary tube or porous element is significant as a limitation on the minimum sampling interval since the entire content of the tube must be taken into the chamber and evacuated before any change in the composition of the gas volume outside the chamber can be detected. This, of course, limits the response of the device to changes in the sample makeup. Moreover, the composition of the gas reaching the chamber may not be the same as that of the volume being investigated because of differential absorption or adsorption, condensation in or on the passage surfaces, or the release or entrainment of components previously so extracted. Minute apertures are difficult to produce with dimensional predictability and, even if of a sufficiently small size, to enable and assist operate with reasonable pumping capacity, they are extremely subject to stoppage by foreign particles in the sample gas. This is a very serious defect where combustion products or possible air pollutants are the subject of the investigation. Pumped manifolds, which are also used, share the above defect of capillary tubes and considerably increase both the complexity of the equipment and their required capacity.

One such prior art system utilizing the two-flow restrictions positioned in the flow stream upstream of the entrance to the vacuum chamber which uses no valving is found in a U.S. Pat. to Riggle et al. No. 2,714,164 issued July 26, 1955. That patent is an example of the sample manifold technique.

Other, earlier attempts at valving techniques for vacuum chambers are found in Hahn et al., U.S. Pat. No. 3,675,072, issued July 4, 1972, which uses a complicated electromagnetic fast closing valve system for emitting samples to a cyclotron, Sodal et al, U.S. Pat. No. 3,895,231, issued July 15, 1975, which utilizes a piezo electric crystal operated needle valve to control these sample gases into a vacuum chamber of a mass spectrometer and Asmus, et al., U.S. Pat. No. 3,483,373, issued Dec. 9, 1969, which utilizes an intermediate airlock chamber.

A single orifice pulse sample system for a mass spectrometer is disclosed in a patent to Bursack, a coinventor in the present application, U.S. Pat. No. 3,992,626, issued Nov. 16, 1976, and assigned to the same assignee as the present application. While by means of that invention, the amount of sample gas introduced into the mass spectrometer can be controlled so as not to exceed the capability of the ion-getter pump and thus the overall pressure within the chamber may be maintained, the sample is still introduced in a definite pulse which results in certain fluctuation in the desired steady state within the high vacuum chamber. This requires the mass spectrometer operation to be coordinated in time with the pulses and causes large pressure fluctuations.

SUMMARY OF THE INVENTION

By means of the present invention, the problems associated with time delays or pulsings in low flow rate sampling for mass spectrometers and the like are solved by the provision of an intermediate chamber between the sample gas and the high vacuum enclosure which, together with connecting orifices, dampens the pulses of a valved inlet to resemble a continuous low-volume flow system. Thus, there is provided a hollow antechamber or cavity disposed between the sample stream and the high vacuum enclosure which connected both with the sample gas and the high vacuum chamber by orifice openings. An electrically operated valve is used to emit a series of volumes of samples by pulses of controlled duration and frequency such that the sample flow from the antechamber into the high vacuum enclosure reamins essentially constant. Thus, while the initial sample is pulsed into the antechamber, the volume of the antechamber enables the sample to leak through the orifice separating it from the high vacuum enclosure at a nearly constant rate. The total flow is controlled such that it does not exceed the capacity of the getter-ion pump in the system. When closed the pulsed aperture forms a vacuum-tight seal, and because its operation is such that the total sample admitted does not exceed the capacity of the getter-ion pump, this enables the device to be completely portable requiring no auxiliary vacuum pumping. Time delays cause by capillary tubes, porous surfaces and the like are eliminated as are other disturbances caused by pressure variations in the systems due to pulsing.

BRIEF DESCRIPTION OF THE DRAWINGS

In the drawings wherein like numerals are utilized to designate like parts throughout the same.

DESCRIPTION OF THE PREFERRED EMBODIMENT

Figure 1:
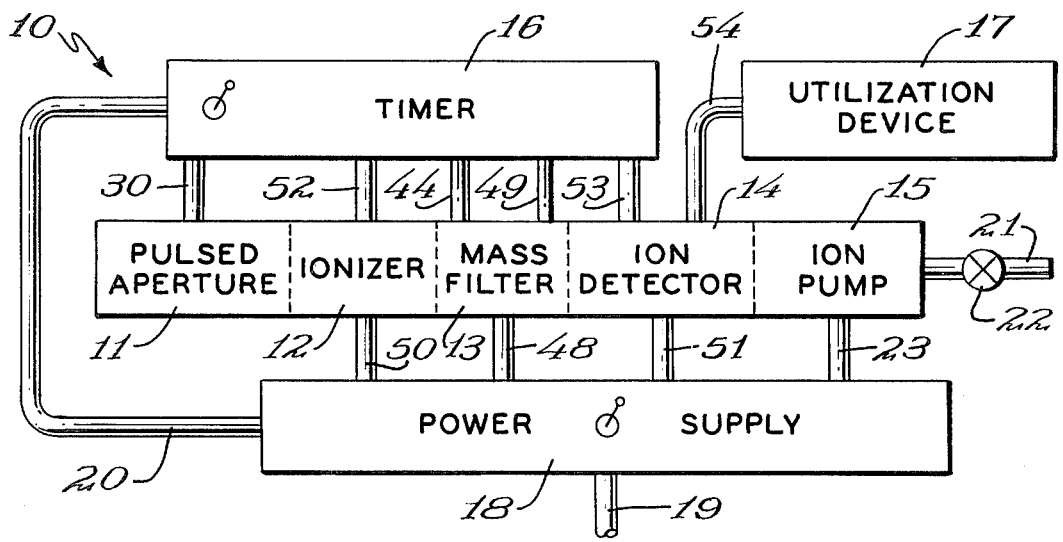
FIG. 1 is a block diagram of a mass spectrometer device including the invention.

The schematic diagram of FIG. 1 shows a mass spectrometer shown generally at 10 having a sampling system 11, and ionizer 12, a mass filter 13, and ion detector 14, and an ion pump 15. These are particularly associated with a vacuum chamber of a mass spectrometer. Associated with the above are a timer 16, a utilization device 17 and a power supply 18. The power supply 18 may be energized in a conventional fashion as through a cable 19 which supplies DC, AC and RF energy to the timer 16 as through a cable 20. The tube 21 is provided having a suitable closure 22 to provide a means for initially evacuating the chamber of the mass spectrometer and bringing the pressure therein down to the working level of the system prior to the admission of any sample gas. This closure, once closed, then provides a vacuum-tight seal in the tubular member 21.

The ion pump 15 is of a well-known construction and operates to remove gas molecules from its environment within the high vacuum enclosure by burying them in a layer of material such a titanium continuously supplied by evaporation from a suitable source. In active gases, the action is primarily one of gettering and titanium has been found to be a particularly suitable getter material for this purpose. For inactive gases, the pump operates to ionize the gas. The ions are then transported by electrostatic or magnetic field attraction to the titanium layer where they are also buried in the continuously depositing titanium. The necessary evaporation and ionizing energy is supplied to the pump 15 as through a conductor 23 from power supply 18.

Pumps of the type described can be constructed, depending on the size, for various gaseous material removing capabilities. In sizing a particular pump, the amount of sample which will be required to be processed in the operation of a mass spectrometer is considered along with the magnitude of the vacuum which will be required in the operation of the elements 12–15 and from this the proper pump capacity may be determined. It must be remembered that the total pressure in the system must not be allowed to rise above a known predetermined amount or it will inversely effect the performance of the components in the mass spectrometer.

Figure 2A:
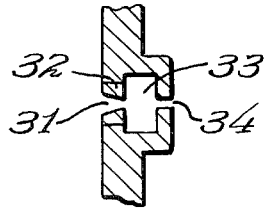
FIG. 2A is an enlarged fragmentary view of the inlet of FIG. 2.
Figure 2:
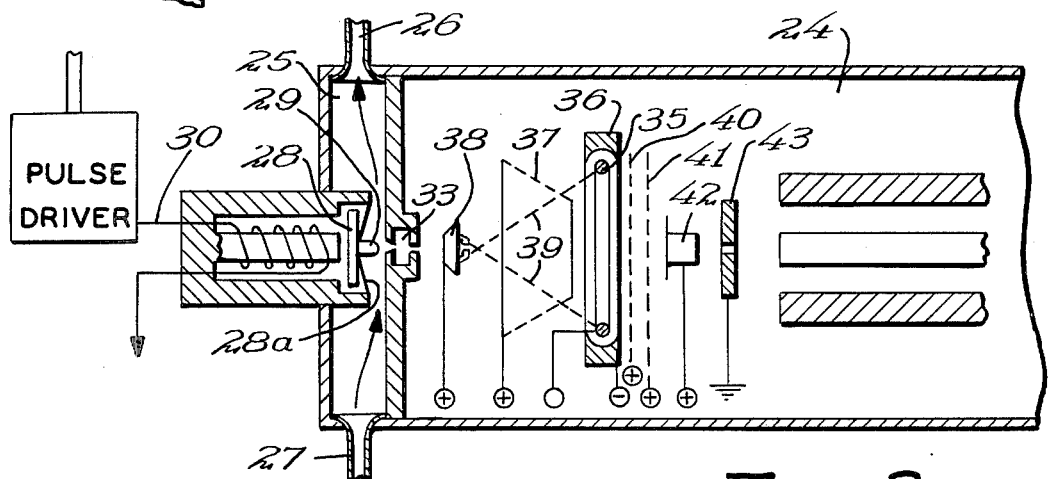
FIG. 2 is a schematic fragmentary cross-section view of a portion of a mass spectrometer showing the sampling system of the invention.

For the purpose of the illustration of the present invention, the fragmentary cross sectional view of FIG. 2 illustrates a typical mass spectrometer chamber equipped with an embodiment of the sampling system of the present invention. The high vacuum enclosure of the mass spectrometer as shown in part at 24 including the ionizer section 12 and the mass filter 13, the sampling system is shown at 11 as integral with the high vacuum enclosure 24.

The sample system includes a sample reservoir 25 which may be open to the ambient atmosphere or connected to a sample source which may be connected in a flow-through manner by connectors 26 and 27. A poppet valve is shown at 28 having an associated retaining spring diaphragm or disc 28a. An electromagnetic valve actuating armature is shown at 29 which associated energizing conductor 30.

The passage between the sample volume 25 and the interior of the vacuum enclosure 24 is shown in greater detail in FIG. 2A and includes an orifice opening 31 having a jewel sealing insert 32, an antechamber cavity 33 and an orifice opening 34 which leads into the enclosure 24. As shown in FIG. 2, when the armature 30 is energized, poppet 28 is attracted disengaging the sealing tip from the jewel orifice 32 opening the passage or orifice 31 thereby allowing an amount of sample gas to enter the antechamber 33. The pressure differential between the chamber 33 and the ambient or sample stream causes the sample to be injected or pulsed into the antechamber. This raises the pressure in the chamber 33 above that of the high vacuum enclosure 24. For a short duration pulse, however, the pressure in the chamber 33, while above that in the high vacuum enclosure 24, remains far below that of the ambient atmosphere. The sample gas then passes into the higher vacuum enclosure 24 through the orifice 34. However, inasmuch as the pressure differential between the antechamber 33 and the high vacuum enclosure 24 is much less than that between the ambient atmosphere and the antechamber 33, the flow through the orifice 34 persists for a longer period than that through the orifice 31.

Figure 3:
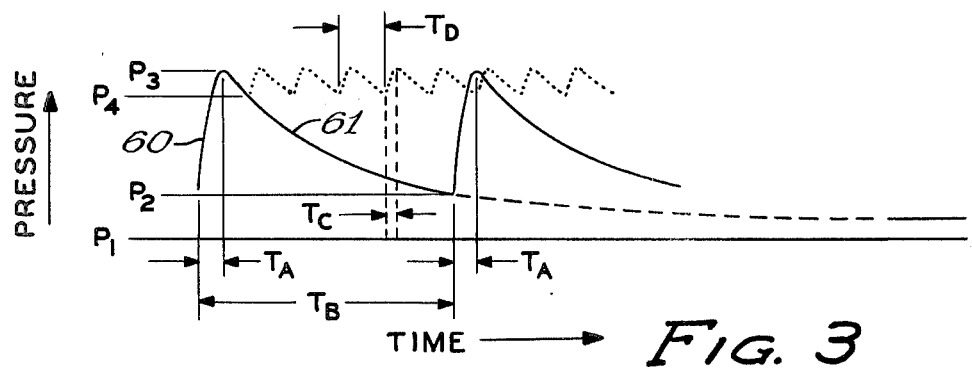
FIG. 3 is a schematic graphical representation of the damping effect of the antechamber of the present invention.

As illustrated in FIG. 3, if the orifice 31 is opened, for example, for a pulse duration $T_A$ at intervals $T_B$ at the first pulse the pressure in the chamber 33 will rise from the initial high vacuum state $P_1$ to a value indicated by $P_3$ as illustrated by the curve at 60. After the initial pulse the pressure will recede according to the line 61 as the sample flows through the orifice 34 into the chamber 24 during the interval between pulses. Thus, pulses of duration $T_A$ of a frequency $T_B$ will produce a pressure variation in which the pressure will rise alternately to $P_3$ and drop to $P_2$. This will produce a corresponding cyclic flow through the orifice 34. If, however, the pulsing frequency is increased and the interval $T_A$ is correspondingly decreased, the cavity pressure in antechamber 33 can be made to stay, for example, in the narrower range of $P_3$ to $P_4$ as illustrated utilizing the pulse interval $T_C$ and frequency $T_D$. This steadier state will result in a much greater uniformity of the flow through the orifice 34. A suitable choice of parameters for pulse duration and frequency for the dimensions of orifices 31 and 34 and the size of the antechamber 33, an essentially constant flow can be achieved across the orifice 34.

In FIG. 2, an annular thermoemissive filament 35 is mounted with respect to annular reflective 36 to emit electrons which travel through a conical accelerating grid 37 to a hollow collector 38. The dotted lines 39 are utilized to represent a cone of electrons on which the entering sample gas inpinges. As a result of that impingement many of the sample gas molecules are ionized. The positive ions are repelled by the positive collector 38 and caused to pass through the annular filament 35. They proceed through a decelerating grid 40, a screen grid 41 and a focussing electrode 42 from which the beam of ions passes through an aperture 43 into mass filter 13.

It is well known that different ions have different mass numbers i.e., different atomic mass units (AMU). The ion detector 14, which may advantageously include an electron-multiplier, is incapable of distinguishing between different ions and merely gives an instantaneous output on cable 54 (FIG. 1) which corresponds to the total number of ions reaching it at any particular instant. As with the other conventional parts of the mass spectrograph, the particular type of mass filter which is used is not material to the invention as the sampling system of the invention be made to arrange to cooperate with the magnetic sector, an omegatron, a time-of-flight filter, a monopole or a quadrupole. The preferred embodiment of the invention shown in the drawing makes use of a quadrupole mass filter which is provided with the necessary RF and DC voltages from the source 20 direct through scale 48 or under the control of timer 16 through cables 44 and 49.

The operation of a quadrupole mass filter is well known and further information on that subject may be found in an article by W. M. Brubaker et al., entitled, "Performance Studies of a Quadrupole Mass Filter," Volume 35, No. 8 of *The Review of Scientific Instruments*, August 1964.

As a further word of explanation, it will be readily understood by those skilled in the use of mass spectrometer devices, the frequency of the RF supplied to filter 13 the ratio of its amplitude to the magnitude of the DC also supplied, determines the AMU number of the ions which the filter permits to pass detector 14. It is also well known that by holding the voltages constant and sweeping the frequency, or by holding the frequency constant and sweeping the voltages while maintaining their ratio constant, the filter will permit ions of regularly increasing (or decreasing) AMU numbers to pass in succession. The electron multiplier output for each sweep is a variable having peaks located in time, relative to the begining of the sweep, in a fashion to identify the materials of serially changing AMU number. The magnitudes of the peaks are representative of amounts of the various materials present in the samples.

Utilizing an undamped pulsing sample inlet of the prior art, a mass filter sweep was required to be initiated with each operation of the single pulse aperture systems. With the more constant flow of the sample produced by the damping effect of the chamber 33, in the present invention, the sweep need not be timed directly to the corresponding pulses and may be operated independently thereof.

The ionizer 12 is shown as energized from power supply 18 through a cable 50. The detector 14 likewise is shown energized through cable 51. Units 12 and 14 may also be energized in accordance with the timer 16 as through cables 52 and 53, respectively.

In operation, at the factory, or prior to use, the tube 21 is connected to a suitable vacuum pump enclosure, 22, when the pressure in the chamber 24 is reduced to a value normally of $10^{-4}$ to $10^{-6}$ torr. The pressure is further reduced by the internal ion pump to a value normally of $10^{-8}$ to $10^{-9}$ torr. The closure 22 is then closed and the unit is disconnected from the pump. It may now be transported to the utilization area without further vacuum pumping. The unit may then be positioned for sampling and a power supply energized.

After a stable condition of the spectrometer is achieved, timer 16 is set in operation, sampling system 11 with ionizer 12 and detector 14 are energized and a voltage or frequency sweep is commenced utilizing the filter 13. The sample gas of interest is caused to pass through the orifice 31 in and through the chamber 33 by means of orifice 34. The frequency and the duration of the pulse combined with the continued operation of the ion pump establishes and maintains the desired pressure within the chamber and stabilizes the stream of ions passing filter 13 for detection. The transit time of ions through the mass filter 13 is in the order of 1 to 10 microseconds. Normally the voltage sweep is initiated at such a value that ions of low AMU numbers pass through the mass filter 13 to the detector 14. The sweep continues enabling successive passage through the filter of those of higher AMU numbers with associated output peaks until the desired range of the instrument has been traversed and the sample completed scanned.

Of course, the utilization device 17 may take any desired form depending on the application of the instrument. It may indicate or record the value of a single peak from among those of a number of peaks within a certain range, or it may even act to control a valve, for example, to maintain the level of a particular material at a particular value.

To insure acceptable leak performance and proper pulsing, finish and alignment of the poppet 28 are important. While poppet finish techniques have included milling and turning followed by soda blast and polishing, turning and polishing have given the best results. In one embodiment poppet 28 was cut to length in a jewelers lathe leaving 0.002 in. of stock for finishing. Two-stage polishing using 600-grit and 4/0 emery paper in which the paper was disk-mounted and turned in the head stock at highest speed followed. The poppet was held in a loosened tail stock which was manually rocked to obtain combined lateral-rotational motion. After polishing, the poppet was cleaned utilizing well-known ultra-sonic techniques with acetone, Freon 113, air-ether spray and installed in the pulsed sampling system. A conservative loading of about 0.7 pounds of the poppet against the jeweled orifice is desirable. Also rotation of the poppet assembly may be required to achieve the best poppet-seat alignment (axial T.I.R. at armature (within 0.001 of 0.002 inch).

Poppet materials have included certain elastomers, plastics or even soft metal such as, for example, aluminum and gold. Among the elastomers, buna-N, adiprene, viton have been promising; among the plastics, vespel and riton show some promise. One successful embodiment utilized a poppet made of teflon which appeared to combine the properties of proper hardness and durability for such use.

The poppet 28, as explained above is held against a jeweled orifice 32 by a spring-diaphragm, or disk 28a which, in turn, is secured to its periphery by a clamp ring (not shown). In one embodiment, the disk was 0.007 inches thick and required about 0.004 inch deflection to obtain 0.75 pound preload. As an alternative to the disk a three-arm spring diaphragm can also be used. One such diaphragm was fabricated from a solid disk of stainless steel by selective etching to leave three spring members joining hub and rim sections. The representative three-arm spring diaphragm had a hub which was 0.25 inches thick and rim and spring members which were 0.013 inches thick. It required about 0.006-inch deflection to obtain a 0.75 preload.

The jeweled orifice insert 32 is preferably of sapphire epoxy-bonded to the adjacent body member. Successful embodiments have also been made utilizing vacuum brazing techniques in which the sapphire orifice was seated in a gold ring which, in turn, was sealed to the adjacent body member.

As has previously been stated, by suitable choice of the parameters proposed to frequency and for the dimension of the orifice 31 antechamber volume 33 and orifice 34 essentially constant flow rate can be achieved into the chamber 24. The substantially constant flow established by this device permit continuous scanning of the sample by the mass spectrometer with no need for synchronization with the pulsed valve system. Thus, unlike previous pulsed leak systems, the scan rate range of the mass spectrometer rendered independent of the pulse rate and the spectrometer may be operated in a continuous asynchronous mode or pulse mode operation can be obtained as desired by adjusting pulse frequency and duration of the pulsed sample system. With this configuration a high data acquisition rate can be obtained to more quickly analyze complex gases containing a multiple of desired species. In addition, a conventional feedback control of the pulse driver which drives the electromagnetic armature 29, can be used to provide automatic control of the vacuum system pressure based on continuous vacuum measurement in the chamber 24.

In one embodiment in that system of the invention the orifices 31 and 34 had a diameter of 0.0024 inches and the antechamber 33 had a volume of $2.4 \times 10^{-5}$ inches$^3$. In another higher low rate embodiment the orifices were 0.013 inches in diameter and the volume 33 0.21 in.$^3$.

One embodiment of a mass spectrograph utilizing the sampling system of the invention had parameters in accordance with Table 1.

TABLE I
TYPICAL ILLUSTRATIVE PARAMETERS

| General | |
|---|---|
| Mass range | 1-65 AMU |
| Resolving power | 100 |
| Sensitivity | 1ppm |
| Volume of chamber 10 | 73.9 cm$^3$ |
| Outside diameter of chamber 10 | 1" |
| Range of pressure in chamber 10 | $10^{-4}$ to $10^{-9}$ torr |
| Detector 14 | electron multiplier |

TABLE I-continued
TYPICAL ILLUSTRATIVE PARAMETERS

| Sampling System 11 | |
|---|---|
| Pulsing rate | 10-50 pulses per second |
| Pulse length | 100 microseconds |
| Aperture bore | .0024" |
| Delivery per pulse | $>3 \times 10^{14}$ molecules |
| Ionizer 12 | |
| Filament 33 (cathode) | 6v 0.25a |
| Aperture 42 | ground |
| Filament 33 | $-100$v |
| Reflector 34 | $-108$v |
| Grid 35 | ground |
| Collector 36 | $+120$v |
| Grid 39 | $+10$v |
| Grid 40 | ground |
| Focus Electrode 41 | $+4$v |
| Energy of output ions | 10ev |

The embodiments of the invention in which an exclusive property or right is claimed are defined as follows:

1. An apparatus for introducing a gaseous sample into an enclosure of high vacuum, such as a mass spectrometer, said apparatus comprising:
   sealing means between a supply of gaseous sample and said enclosure of high vacuum said sealing means further comprising an enlarged hollow cavity forming an antechamber between said enclosure of high vacuum and said gaseous sample supply said cavity having a first opening therein in comunication with said gaseous sample for admitting amounts of said gaseous sample into said antechamber and a second opening in said antechamber in communication with said enclosure of high vacuum allowing the passage of said sample into said enclosure of high vacuum;
   closure means for closing said first opening; and
   means for operating said closure means such that pulses of said gaseous sample are admitted to said antechamber of a predetermined duration and frequency in such a manner to provide a substantially steady state flow condition into said enclosure of high vacuum.

2. The apparatus of claim 1 wherein said volume of high vacuum is a mass spectrometer and said sealing means is integral with the sampling system therefor.

3. The apparatus of claim 1 wherein said closure means is a poppet valve and said means for operating said closure means comprises an electromagnetic valve operator.

4. The apparatus of claim 1 wherein the duration and frequency of the operation of said closure means in conjunction with the volume of said hollow antechamber and said opening therein are such that the sample flow into said volume of high vacuum remains substantially constant.

* * * * *